US012805908B2

(12) United States Patent
Fabri et al.

(10) Patent No.: US 12,805,908 B2
(45) Date of Patent: Nov. 24, 2026

(54) CLAMP OF EXTERNAL FIXATION DEVICE

(71) Applicant: CITIEFFE S.r.l., Calderara di Reno (IT)

(72) Inventors: Francesco Fabri, Calderara di Reno (IT); Alan Dovesi, Calderara di Reno (IT)

(73) Assignee: CITIEFFEE S.R.L., Calderara di Reno (IT)

( * ) Notice: Subject to any disclaimer, the term of this patent is extended or adjusted under 35 U.S.C. 154(b) by 0 days.

(21) Appl. No.: 18/636,877

(22) Filed: Apr. 16, 2024

(65) Prior Publication Data

US 2024/0341812 A1 Oct. 17, 2024

(30) Foreign Application Priority Data

Apr. 17, 2023 (IT) ........................ 102023000007383

(51) Int. Cl.
*A61B 17/64* (2006.01)

(52) U.S. Cl.
CPC ...... *A61B 17/6466* (2013.01); *A61B 17/6416* (2013.01)

(58) Field of Classification Search
None
See application file for complete search history.

(56) References Cited

U.S. PATENT DOCUMENTS 6,428,540 B1 8/2002 Claes
6,565,564 B2 * 5/2003 Hoffman ............ A61B 17/6466 606/59
6,716,212 B1 4/2004 Pickens
9,962,187 B2 * 5/2018 Erickson ............ A61B 17/6458
10,206,713 B2 * 2/2019 Olsen ................. A61B 17/6458
2004/0193156 A1 * 9/2004 Waisman ............. A61B 17/742 606/60
2006/0229604 A1 * 10/2006 Olsen ................. A61B 17/6425 606/54
2011/0066151 A1 * 3/2011 Murner ............. A61B 17/6466 606/54
2012/0089142 A1 * 4/2012 Mullaney ........... A61B 17/6466 606/54
2012/0209264 A1 8/2012 Zandona
2016/0038184 A1 * 2/2016 Erickson ............ A61B 17/6425 606/59
2016/0199098 A1 * 7/2016 Slagle ................ A61B 17/6458 606/59
2016/0278812 A1 * 9/2016 Riccione ............ A61B 17/6416
(Continued)

FOREIGN PATENT DOCUMENTS

CN 109009370 A 12/2018
EP 0383419 A1 * 8/1990 ........... A61B 17/645
WO 2022090410 A1 5/2022

OTHER PUBLICATIONS

Italian Search Report dated Nov. 8, 2023 from counterpart Italian App No. IT 202300007383.

*Primary Examiner* — Jan Christopher L Merene
(74) *Attorney, Agent, or Firm* — SHUTTLEWORTH & INGERSOLL, PLC; Timothy J. Klima

(57) ABSTRACT

Described is a clamp of an external fixation device for the treatment of bone fractures, including a first locking unit designed to lock two bone screws, a second locking unit and a third locking unit each designed to lock a respective connecting bar.

1 Claim, 4 Drawing Sheets

(56) References Cited

U.S. PATENT DOCUMENTS

| | | | | |
|---|---|---|---|---|
| 2024/0058037 | A1* | 2/2024 | Meiggs .............. | A61B 17/6466 |
| 2024/0122624 | A1* | 4/2024 | Rush .................. | A61B 17/6425 |
| 2024/0225698 | A1* | 7/2024 | Smyth ................ | A61B 17/6475 |
| 2024/0225699 | A1* | 7/2024 | Smyth ................ | A61B 17/6466 |

* cited by examiner

CLAMP OF EXTERNAL FIXATION DEVICE

This application claims priority to Italian Patent Application 102023000007383 filed Apr. 17, 2023, the entirety of which is incorporated by reference herein.

This invention relates to external orthopaedic fixation devices.

In particular, the invention relates to a clamp of an orthopaedic external fixation device.

Over recent years, in orthopaedics, a technique has been widespread for stabilising fractures, especially in the long bones of the limbs, which does not need to make use of traditional plaster casts, using the so-called external fixation devices instead.

External fixation devices usually comprise a plurality of bone screws which are implanted in the bone stumps of the fracture in such a way that the head ends of the screws project from the skin of the patient. These ends are anchored to a rigid external frame which is fitted with bars, clamps and joints which can be oriented so as to be adapted to the position of the screws. In its most widespread versions, the bars making up the frame have a cylindrical cross-section and are positioned longitudinally.

The screws usually have a cylindrical body, having, on one side, a threaded portion intended to be screwed into the bone stump and, on the other side, the above-mentioned head end, which is shaped to be able to be coupled to a grip which allows the screw to be screwed into the bone stump.

Operatively, after making an incision in the soft tissue, the surgeon makes holes in the bone stumps on opposite sides of the fracture fissure and implants the screws in the holes.

The surgeon then couples the screws, without the temporary grip attached, to the respective clamps of the frame; then, where necessary and possible, the edges of the fracture are aligned in such a way as to position the bone stumps in the most suitable position to knit together.

Once the fracture has been reduced, the surgeon connects and locks the joints and clamps using the above-mentioned longitudinal bars, to keep the bone stumps in the predetermined position, thus allowing the correct formation between the bone stumps of "bone callus", which progressively restores the lamellar bone tissue with which the bone recovers its original continuity and functionality.

The external fixation devices allow, with a hold on the bone reasonably distant from the fracture centre and with a stabilisation and adjustability outside of the fracture, action to be taken on the bone stumps whilst at the same time leaving the fracture zone free for surface medication.

At the same time, external fixation devices do not interfere with the aeration of the fractured part and reduce the loss of muscle tone normally encountered with the use of plaster casts.

Several years ago, the use of external fixation devices was extended to a vast range of orthopaedic operations, such as limb lengthening, correction of bone axis rotary and angular deformities, pseudarthrosis, etc.

In other words, the external fixation devices are currently used in orthopaedics, both to correct deformations caused by trauma and to correct pathological deformations.

Although universally used in the orthopaedic field, prior art external fixation devices have not always been found to be adequate in some cases of long bone fractures.

In particular, for example, as often occurs in the case of the tibia, when the fracture is located close to its proximal end close to the tibial plateau, it may be difficult for the surgeon to position several screws in the smaller stump.

In short, given the reduced space in the longitudinal direction, it may not be easy to implant two or more screws and simultaneously connect them to the respective clamps of the frame for fastening the latter to the respective longitudinal bars.

The aim of this invention is to provide a clamp for an external fixation device for treating bone fractures which is able to overcome the drawbacks of the prior art and which is at once simple and inexpensive to make and practical to use.

A further aim is to provide a clamp for an external fixation device which allows a practical application of screws and clamps even in the case of stumps with limited longitudinal extension.

Yet another aim of this invention is to provide a clamp for an external fixation device which allows effective handling by the user, also allowing extreme versatility of use.

The technical features of the invention, according to the above-mentioned aims, are clearly described in the appended claims and its advantages are apparent from the detailed description which follows, with reference to the accompanying drawings which illustrate a non-limiting example embodiment of it, and in which:

Figure 1:
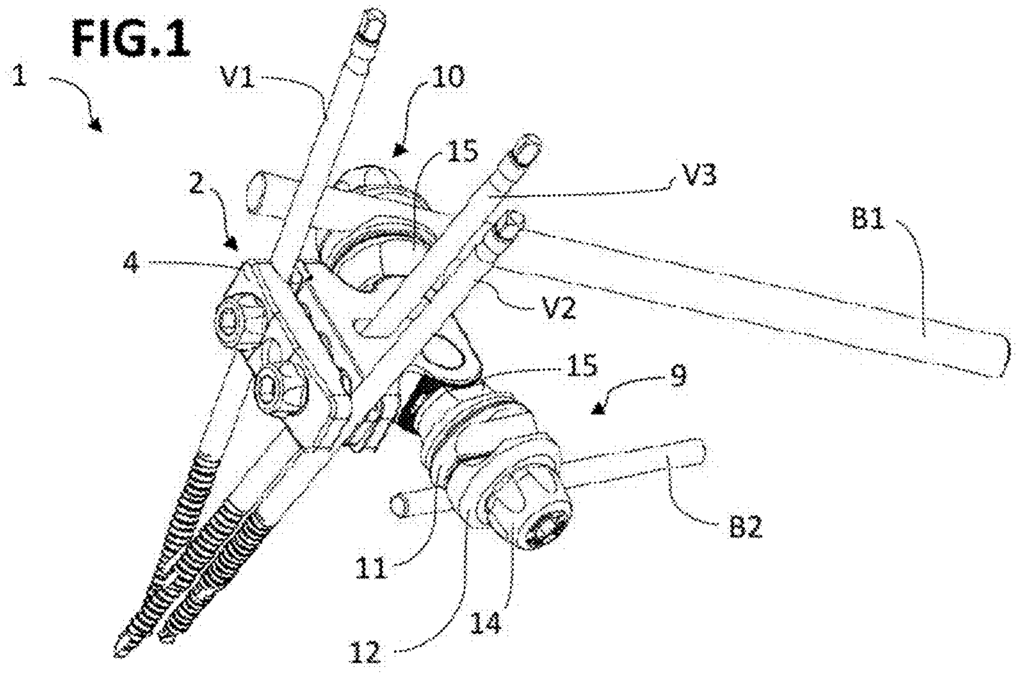
FIG. 1 is a schematic perspective view of an embodiment of the clamp of the external fixation device according to this invention, in a configuration of use.

As illustrated in FIG. 1, the numeral 1 denotes in its entirety a clamp for an external fixation device for treating bone fractures made in accordance with this invention.

The clamp 1 of an external fixation device, hereinafter denoted for brevity also merely as clamp 1, is designed to stably connect, in the context of an external fixation device, not illustrated in its entirety, respective bone screws V1, V2, V3 to longitudinal connecting bars B1, B2, both of these of known type.

With reference to FIG. 1, the clamp 1 comprises a first locking unit 2 designed to lock two bone screws V1, V2.

As described in more detail below, the first locking unit 2 is designed to lock the two bone screws V1, V2 in the same plane P, the tracks of which are perpendicular to the respective planes shown in FIGS. 2, 3 and 5.

The first locking unit 2 comprises a central body 3 and a first jaw 4 which is movable relative to the central body 3 for locking the above-mentioned two bone screws V1, V2 in contact with the central body 3.

Figure 5:
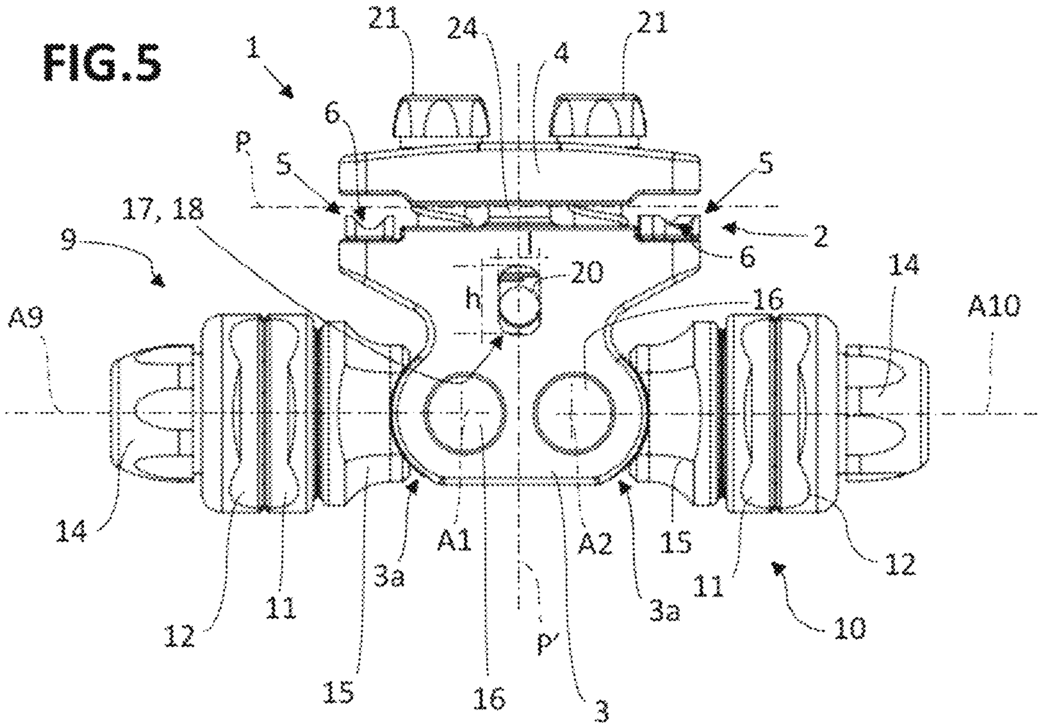
FIG. 5 is a schematic top plan view of the clamp for an external fixation device in accordance with this invention.
Figure 6:
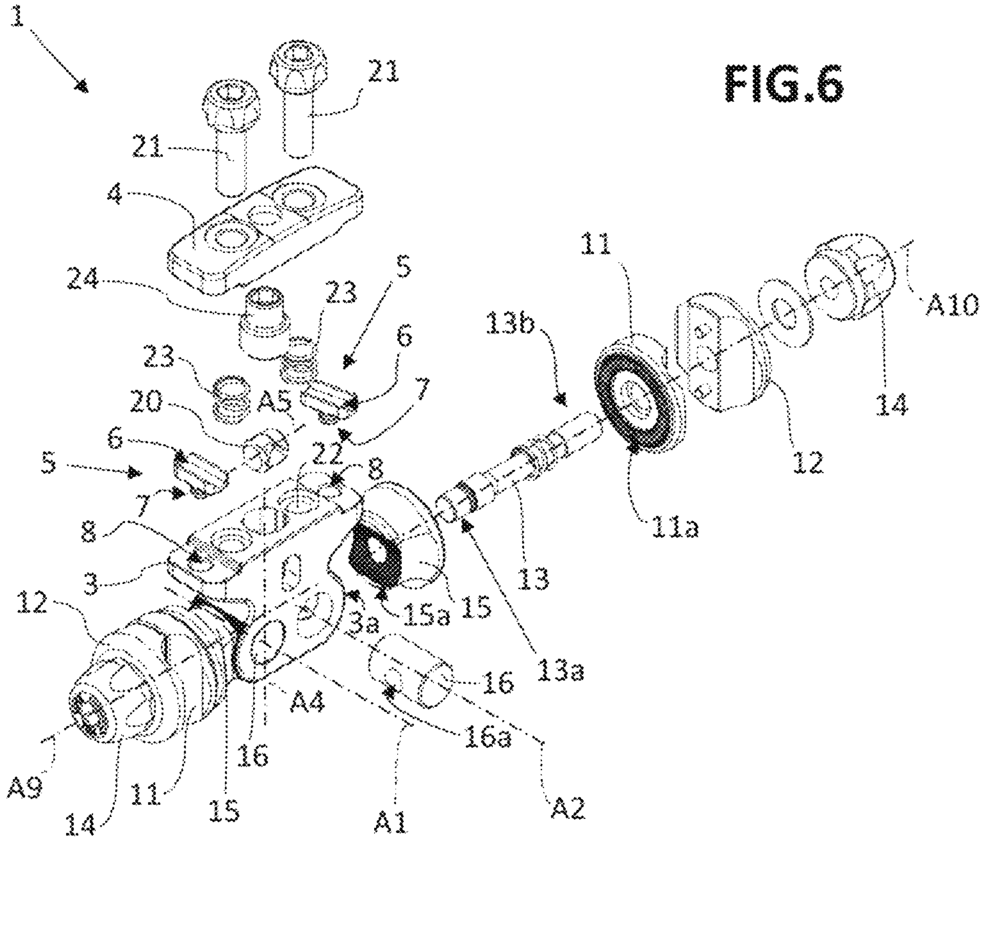
FIGS. 6 and 7 are partly exploded perspective views, from different angles, of the clamp of FIG. 5.

As illustrated in detail in FIGS. 5 and 6, the first locking unit 2 comprises, interposed between the central body 3 and the first jaw 4, respective housings 5 for the two bone screws V1, V2.

Figure 7:
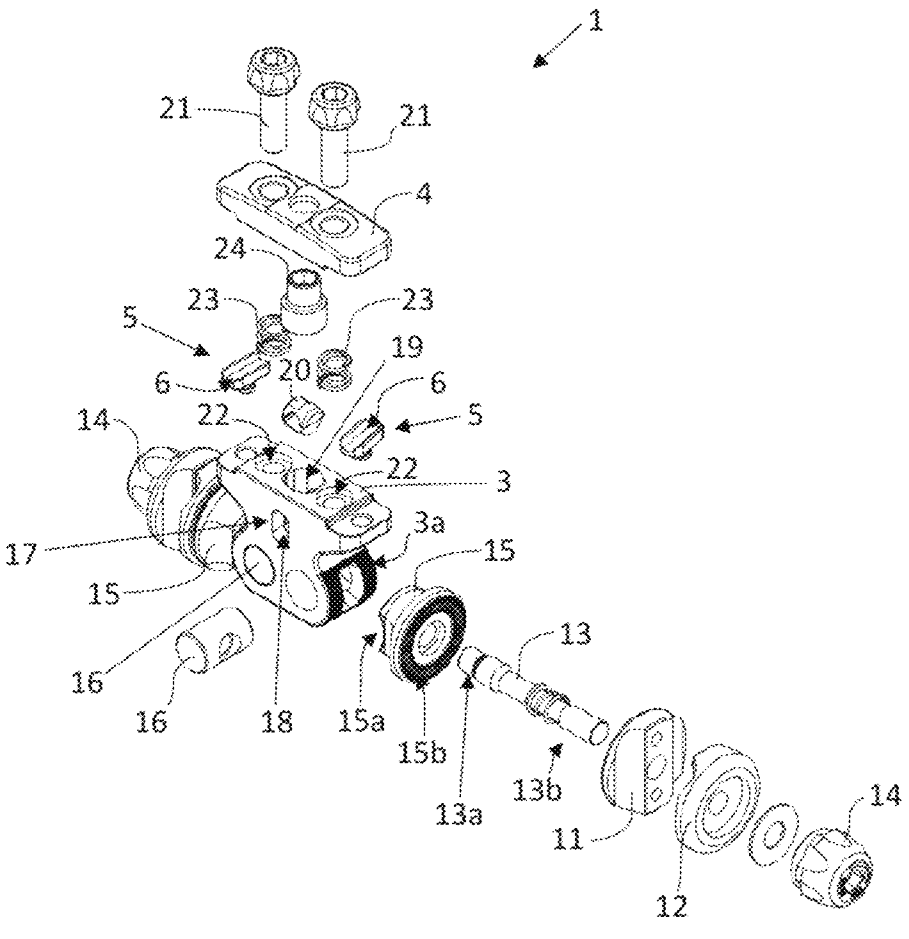

As clearly shown in FIGS. 6 and 7, the housings 5 have a concave portion 6 shaped to match the body of the bone screws V1, V2 and a pin 7 designed to be inserted in a respective hole 8 made in the central body 3 so that the housing 5 oscillates with respect to the central body 3 according to an axis of oscillation perpendicular to the above-mentioned plane P on which it lies.

Figure 4:
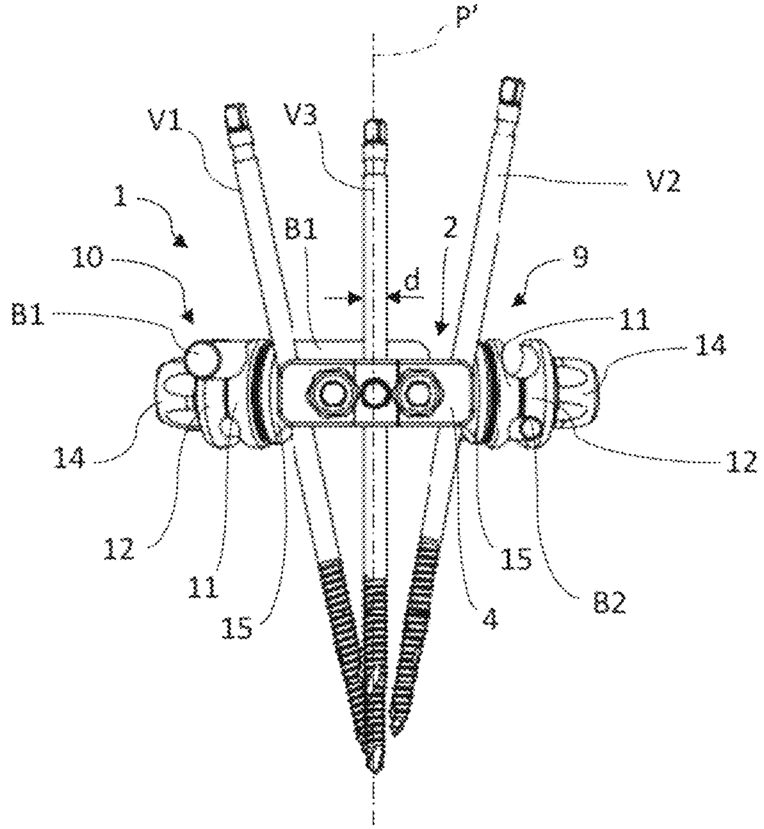
FIG. 4 is a schematic front elevation view of the clamp of the preceding drawings.

This means that the housings 5 are configured to allow the bone screws V1, V2 to be inclined in the above-mentioned plane P in which they lie, as illustrated in FIG. 4, where the two bone screws V1, V2 are clearly not parallel to each other.

The fact of being able to incline independently in the plane P each of the two bone screws V1, V2 allows the surgeon a wide possibility of choosing their best position with respect to the bone stump on which they engage.

The clamp 1 comprises a second locking unit 9 and a third locking unit 10 each designed to lock a respective connecting bar B1, B2.

Each of the second and third locking units 9, 10 comprises a respective second jaw 11 and a respective third jaw 12 designed to act in conjunction with each other to clamp in contact a respective connecting bar B1, B2.

Figure 2:
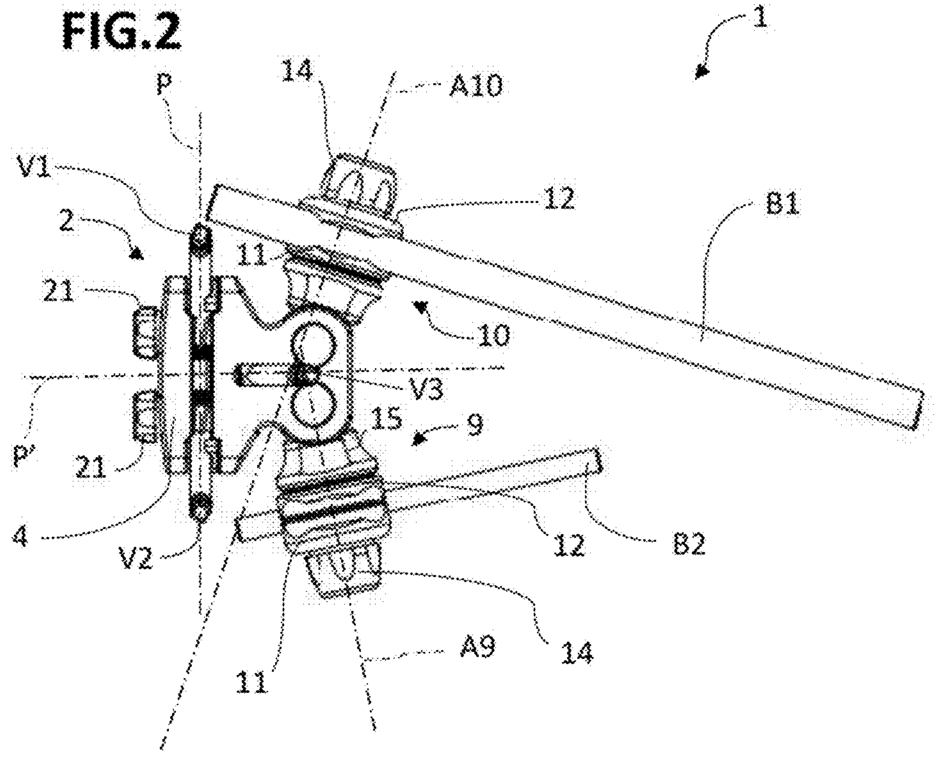
FIG. 2 is a schematic plan view from above of the clamp of FIG. 1.
Figure 3:
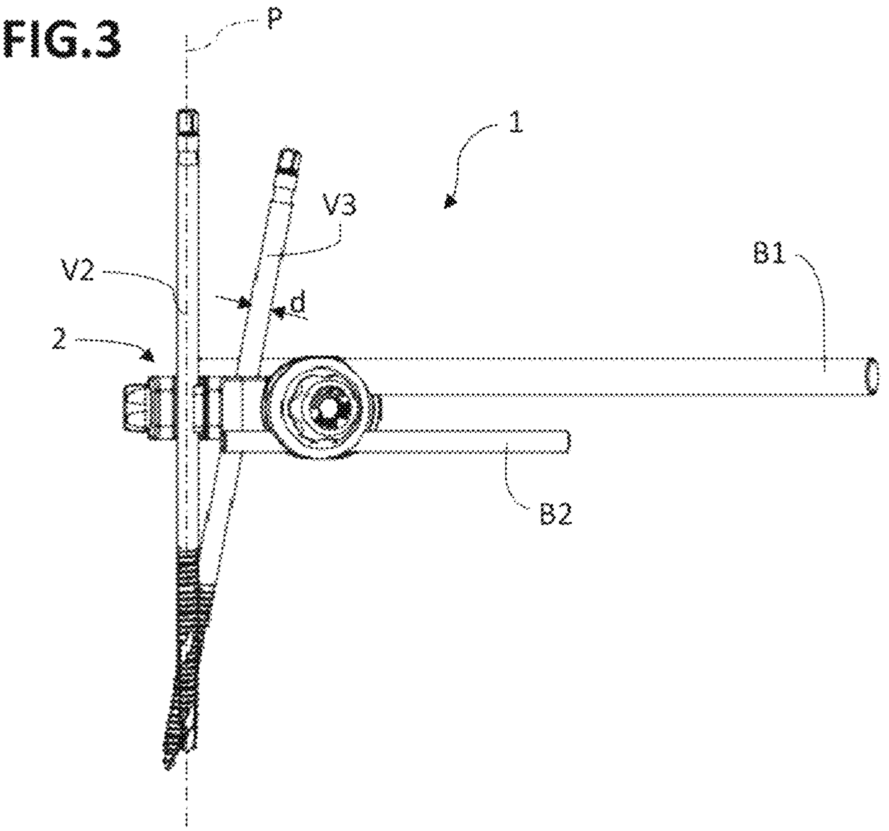
FIG. 3 is a schematic side elevation view of the clamp of the preceding drawings.

The connecting bars B1, B2 are shown in the accompanying FIGS. 1 to 3 with different diameters so as to clarify the attitude of the second and third jaws 11, 12 to engage connecting bars of different diameters.

As illustrated in FIGS. 5 to 7, the above-mentioned second and third locking units 9, 10 are supported by the central body 3 and are connected rotatably to it.

More in detail, the second 9 and third 10 locking units are pivoted on the central body 3 so as to oscillate about respective axes A1, A2 parallel to said plane P on which it lies.

As shown in FIGS. 6 and 7, each of the above-mentioned second and third locking units 9, 10 comprises a rod-shaped element 13, threaded at relative end portions 13*a*, 13*b*, which extends longitudinally through the above-mentioned respective second and third jaws 11, 12 according to a predetermined central axis A9, A10 of each of the second and third locking units 9, 10.

The second and third locking units 9, 10 also comprise respective fastening means 14 which engage by screwing with a corresponding respective rod-shaped element 13 for fastening the second and third jaws 11, 12 both to each other and in contact with the central body 3.

The second and third locking units 9, 10 comprise, interposed between the second jaw 11 and the central body 3, a respective base element 15, which is also passed through centrally by the above-mentioned rod-shaped element 13.

With reference to FIGS. 6 and 7, the base element 15 of each of the locking units 9, 10 has a concave curved proximal face 15*a* which couples with a corresponding convex curved face 3*a* shaped to match, made on the central body 3.

More in detail, as clearly illustrated in FIG. 5, the central body 3 has two convex curved faces 3*a* having curvatures respectively concentric with the two axes A1, A2 of oscillation of the second and third locking units 9, 10.

The surfaces of the above-mentioned curved concave face 15*a* and convex face 3*a* are of the anti-rotation type, advantageously made with interpenetrating scoring designed to prevent reciprocal rotation when in contact with each other.

Due to the above-mentioned scoring made on their respective surfaces, the curved faces 3*a*, 15*a* are basically splined.

More in detail, the above-mentioned curved splined faces 3*a* made in the central body 3 are respectively defined by a cylindrical sector having a respective axis coinciding with each of the axes A1, A2 of oscillation of the second and third locking units 9, 10.

Similar anti-rotation surfaces are made, respectively, on the face 15*b* of the base element 15 and on the face 11*a* of the second jaw 11, the faces 15*b*, 11*a* being in use in contact, and similarly, also in this case, the surfaces made with splines are designed to prevent, when clamped, the reciprocal rotation of the two elements relative to the respective central axis A9, A10.

As illustrated in FIGS. 5 to 7, the clamp 1 also comprises for each of the second and third locking units 9, 10 a respective pin 16 inserted rotatably in a respective hole made in the central body 3.

The pins 16 define, for the two second and third locking units 9, 10, respective pivot elements for their oscillation about the axes A2, A3.

The two pins 16 have, with a diametric trend, respective threaded through holes 16*a* in which holes 16*a* engage by screwing the rod-shaped elements 13 with the respective proximal end portions 13*a*.

As illustrated in FIGS. 5 and 6, the first locking unit 2 comprises two screws 21 which engage by screwing inside respective threaded holes 22 made in the central body 3.

A respective helical spring 23 is positioned wound about each of the above-mentioned screws 21, interposed between the central body 3 and the first jaw 4 to perform an action opposing the clamping of the first jaw 4 on the central body 3.

With reference to the accompanying drawings, the clamp 1 according to this invention advantageously comprises a seat 17 designed to house a third bone screw V3.

As clearly illustrated in FIGS. 1 to 3, the third bone screw V3 is not positioned in the above-mentioned plane P in which the bone screws V1 and V2 lie.

On the other hand, the above-mentioned seat 17 is configured to allow the inclination of the third bone screw V3 on a plane P' at a right angle to the above-mentioned plane P on which it lies.

The tracks of the plane P', perpendicular to the respective planes of the drawing, are visible in FIGS. 2, 4 and 5.

More in detail, as illustrated in FIGS. 6 and 7, the seat 17 is formed by a first through hole 18 in the direction of the axes A1, A2 through which the third bone screw V3 is inserted and by a second blind hole 19 having a central axis A4, transversal to the first through hole 18.

As illustrated in FIG. 5, viewed from above, the first through hole 18 has an approximately rectangular shape, with a short side I just greater than the diameter d of the third bone screw V3 and a long side much greater than the diameter d.

The clamp 1 comprises a cylindrical element 20 for guiding the third bone screw V3, the cylindrical guide element 20 being inserted in the second blind hole 19 in such a way as to be positioned with its central axis A5 transversal to the axis A4 of the second blind hole 19, and being free to rotate inside the second blind hole 19 about its own axis A5.

The cylindrical guide element 20 has a diametric through hole which is designed to slidably engage the third bone screw V3.

Advantageously, the above-mentioned through hole is made open, meaning that there is a gap in material which prevents the inner cylindrical surface of the hole from extending for 360°.

The fact that the cylindrical guide element 20 can rotate about its axis A5 inside the second blind hole 19, together with the fact that the first through hole 18 has a rectangular extension, with a long side h much greater than the diameter d of the third bone screw V3, makes it possible to incline the third bone screw V3 in the plane P' by a predetermined angle.

The possibility of inclining the third bone screw V3 is therefore useful for the surgeon who may therefore have a further degree of freedom in the connection of the clamp 1 to a bone stump.

As illustrated in FIGS. 6 and 7, the clamp 1 comprises a screw 24, located at the seat 17, for braking the rotation of the cylindrical element 20.

The brake screw 24 is engaged by screwing in the second blind hole 19, the inner surface of which is therefore at least partly threaded.

The brake screw 24, together with the cylindrical guide element 20, define, for the clamp 1, respective clamping means designed to stably fix the third bone screw V3 according to the desired inclination.

In use, in the example configuration of use illustrated in FIGS. 1 to 4, the clamp 1 has the first locking unit 2 which engages the bone screws V1 and V2 positioned converging towards an engagement zone, not illustrated, of a bone stump.

The bone screws V1 and V2 are illustrated converging, in order to show the possibility of them being inclined by a predetermined angle on the plane P on which they lie, due to the presence of the housings 5 which can rotate by the above-mentioned predetermined angle relative to the central body 3.

In effect, the housings 5 comprise a concave cradle-shaped portion 6 for slidably housing a bone screw V1, V2, and an underlying pin 7 which rotatably engages in the respective hole 8.

The rotation of the housings 5 determines a corresponding guided inclination of the bone screws V1, V2 in their plane P.

In other words, the concave shape of the portions 6, since it is shaped to match the stem of the bone screws V1, V2, is integral with the latter during their inclination in the plane P in which it lies, thus guaranteeing a stable positioning of the bone screws V1, V2 when the first jaw 4 is tightened against the central body 3 by tightening the screws 21.

The third bone screw V3 is similarly positioned in the seat 17, slidably engaged in the respective cylindrical guide element 20, which is designed to rotate on its central axis, inside the second blind hole 19, to adapt to the desired inclination of the third bone screw V3 in the respective plane P'.

After reaching the desired inclination of the third bone screw V3, the surgeon can tighten the brake screw 24, which by pushing on the cylindrical guide element 20 causes it to stop relative to rotation and sliding or slipping. At the same time, since the cylindrical guiding element 20 has the above-mentioned diametrically through hole open, a pressure applied on it determines, with a local deformation, a sort of pincer closure of the cylindrical element 20 on the stem of the third bone screw V3 which is therefore blocked even in a slidable fashion.

With regard to the second and third locking units 9, 10, on the other hand, they offer both the possibility of oscillating about the axes A1, A2, and the possibility of rotating about the axes A9, A10, to guarantee the maximum adaptability to the needs of the surgeon in the arrangement of the connecting bars B1, B2 and, therefore, in the stable connection of the clamps.

The clamp 1 according to the invention overcomes the above-mentioned drawbacks and brings important advantages.

A first advantage connected to the invention is due to the fact that it offers an extremely versatile clamp in which it is possible to operate in a substantially independent manner on several bone screws and also on the locking units of the longitudinal elements, maintaining an extremely practical use, and being simple and intuitive for the operator.

In particular, the possibility of inclining the bone screws V1 and V2 at desired angles in the plane P in which they lie is extremely advantageous, allowing the surgeon who applies the fixing device a great versatility in choosing the fixing point for the screws V1, V2.

It should therefore be noted how the clamp according to this invention has the advantage of allowing independent locking of the bone screws and of the longitudinal elements.

The bone screws V1, V2 can also be advantageously locked irrespective of the third bone screw V3.

The invention claimed is:

1. A clamp of an external fixation device for the treatment of bone fractures, comprising:

a first locking unit configured to lock first and second bone screws in a first plane, said first locking unit comprising a central body and a first jaw which is movable relative to said central body for locking said first and second bone screws in contact with said central body, a second and a third locking unit each configured to lock a respective connecting bar, each of said second locking unit and third locking unit comprising a second jaw and a third jaw configured to act in conjunction with each other to clamp in contact a respective connecting bar, said second and third locking units being supported by said central body and rotatably connected to said central body;

wherein said second and third locking units are pivoted on said central body to oscillate about respective axes of oscillation parallel to said first plane;

wherein each of said second and third locking units comprises a rod-shaped element at least partly threaded extending longitudinally through said respective second and third jaws according to a predetermined central axis of said second and third locking units, and a clamping member engaging by threading with said rod-shaped element to clamp the second and third jaws to each other and to said central body;

wherein each of said second and third locking units is pivoted on said central body by a respective pin, wherein each of said rod-shaped elements is threaded stably with a relative end to a respective pin.

* * * * *